United States Patent
Barraza-Bernal et al.

(10) Patent No.: US 10,405,742 B2
(45) Date of Patent: Sep. 10, 2019

(54) APPARATUS FOR ASSISTING IN ESTABLISHING A CORRECTION FOR CORRECTING HETEROTROPIA OR HETEROPHORIA AND METHOD OF OPERATING A COMPUTER FOR ASSISTING IN ESTABLISHING A CORRECTION FOR CORRECTING HETEROTROPIA OR HETEROPHORIA

(71) Applicant: Carl Zeiss Vision International GmbH, Aalen (DE)

(72) Inventors: Maria Jose Barraza-Bernal, Aalen (DE); Siegfried Wahl, Donzdorf (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 16/353,027

(22) Filed: Mar. 14, 2019

(65) Prior Publication Data
US 2019/0209005 A1 Jul. 11, 2019

Related U.S. Application Data

(63) Continuation of application No. PCT/EP2017/072633, filed on Sep. 8, 2017.

(30) Foreign Application Priority Data

Sep. 15, 2016 (EP) ..................... 16188905

(51) Int. Cl.
*A61B 3/103* (2006.01)
*A61B 3/00* (2006.01)
(Continued)

(52) U.S. Cl.
CPC ............ *A61B 3/103* (2013.01); *A61B 3/0058* (2013.01); *A61B 3/08* (2013.01); *A61B 3/085* (2013.01);
(Continued)

(58) Field of Classification Search
CPC ............ A61B 3/08; A61B 3/085; A61B 3/103
(Continued)

(56) References Cited

U.S. PATENT DOCUMENTS 5,094,521 A 3/1992 Jolson et al.
7,597,445 B2 * 10/2009 Sakurada ................. A61B 3/08
351/243
(Continued)

FOREIGN PATENT DOCUMENTS

CN 101147670 A 3/2008
DE 102008015189 A1 10/2009
(Continued)

OTHER PUBLICATIONS

Preslan et al. "Baltimore Vision Screening Project," Ophthalmology, 103(1), pp. 105 to 109, Jan. 1996.
(Continued)

*Primary Examiner* — Zachary W Wilkes
(74) *Attorney, Agent, or Firm* — Ewers & Hasselmann PLLC (57) ABSTRACT

An apparatus for assisting in establishing a correction for correcting heterotropia or heterophoria is disclosed. The apparatus tests a prescription for correcting the heterotropia or heterophoria before the prescription is actually realized. The apparatus includes a simulation device with an input interface, a generator unit, and a viewing device. The input interface receives diagnostic data, classification data, and magnitude data concerning the heterotropia or heterophoria, and prescription data indicating a suitable prism. The generator unit generates a right simulation image for the right eye and a left simulation image for the left eye, wherein the right and left simulation images each represent the same object or scene looked at by the respective viewing angles of the eyes. The viewing device has separate displays or
(Continued)

display sections for displaying the simulation image to the right eye and the left eye of the patient.

13 Claims, 3 Drawing Sheets

(51) Int. Cl.
*A61B 3/08* (2006.01)
*A61B 3/18* (2006.01)
*A61B 3/04* (2006.01)
*G02B 27/00* (2006.01)
*A61B 5/16* (2006.01)
*G06F 3/01* (2006.01)
*G02B 27/01* (2006.01)

(52) U.S. Cl.
CPC ............. *A61B 3/18* (2013.01); *A61B 5/163* (2017.08); *G02B 27/0172* (2013.01); *G06F 3/012* (2013.01); *G06F 3/013* (2013.01); *A61B 3/0091* (2013.01); *A61B 3/04* (2013.01); *G02B 27/0093* (2013.01); *G02B 2027/0134* (2013.01)

(58) Field of Classification Search
USPC ................................. 351/201, 205, 227, 246
See application file for complete search history.

(56) References Cited

U.S. PATENT DOCUMENTS

| | | | |
|---|---|---|---|
| 9,492,075 B2* | 11/2016 | Schroth | A61B 3/085 |
| 9,921,418 B2* | 3/2018 | Hatanaka | G02C 7/027 |
| 2009/0153796 A1* | 6/2009 | Rabner | A61B 3/0091 |
| | | | 351/201 |
| 2011/0208493 A1 | 8/2011 | Altheimer et al. | |
| 2012/0287398 A1* | 11/2012 | Baker | A61B 3/103 |
| | | | 351/201 |
| 2015/0163480 A1 | 6/2015 | Qi et al. | |
| 2017/0052389 A1 | 2/2017 | Hatanaka | |
| 2018/0028057 A1 | 2/2018 | Oz et al. | |

FOREIGN PATENT DOCUMENTS

| | | |
|---|---|---|
| EP | 2856931 A1 | 4/2015 |
| EP | 3109694 A1 | 12/2016 |
| WO | 2015125848 A1 | 8/2015 |
| WO | 2016139662 A1 | 9/2016 |

OTHER PUBLICATIONS

Bennett & Rabbetts: "Anomalies of Binocular Vision: heterotropia or heterophoria," in Clinical Visual Optics, 3rd edition, pp. 167 to 190, 1998.

Matsuo et al.: "The Prevalence of Strabismus and Amblyopia in Japanese Elementary School Children," Ophthalmic Epidemiol. 12(1), pp. 31 to 36, Feb. 2005.

Matsuo et al.: "Comparison of prevalence rates of strabismus and amblyopia in Japanese elementary school children between the years 2003 and 2005," Acta Med Okayama 61 (6), pp. 329 to 334, , Dec. 2007.

Williams et al: "Prevalence and risk factors for common vision problems in children: data from the ALSPAC study," Br J Ophthalmol. 92(7), pp. 959 to 964, Jul. 2008.

Giordano et al.: "Prevalence of strabismus and amblyopia in preschool-aged children: The Baltimore Pediatric Eye Disease Study," Invest Ophthalmol Vis Sci., 49, E-Abstract 1552, 2008.

Garvey et al.: "Prevalence of strabismus among preschool, kindergarten, and first-grade Tohono O'odham children," Optometry 81, pp. 194 to 199, 2010.

Din En Iso "Ophthalmic Optics—Spectacle Lenses—Vocabulary," Oct. 2013.

European Search Report issued in European patent application 16188905.0, to which this application claims priority, dated Mar. 28, 2017.

International Preliminary Report on Patentability issued in PCT/EP2017/072633, to which this application claims priority, dated Jan. 28, 2019.

* cited by examiner

APPARATUS FOR ASSISTING IN ESTABLISHING A CORRECTION FOR CORRECTING HETEROTROPIA OR HETEROPHORIA AND METHOD OF OPERATING A COMPUTER FOR ASSISTING IN ESTABLISHING A CORRECTION FOR CORRECTING HETEROTROPIA OR HETEROPHORIA

CROSS REFERENCE TO RELATED APPLICATIONS

This application is a continuation application of international application PCT/EP2017/072633, filed Sep. 8, 2017, which claims priority to European patent application EP 16188905.0, filed Sep. 15, 2016, both of which are hereby incorporated by reference in their entireties.

TECHNICAL FIELD

The present disclosure relates to an apparatus for assisting in establishing a correction for correcting heterotropia or heterophoria. In addition, the disclosure relates to a method of operating a computer for assisting in establishing a correction for correcting heterotropia or heterophoria and a computer program product.

BACKGROUND

Binocular vision, or the use of two eyes working in conjunction, can be achieved only with a well-developed, coordinated oculomotor and neural system and with the optical functioning of each eye in reasonable adjustment. When some of the mentioned mechanisms fail, binocular vision can be impaired, as it is described by Bennett & Rabbetts 1998, Clinical Visual Optics, $3^{rd}$ edition.

Figure 1:
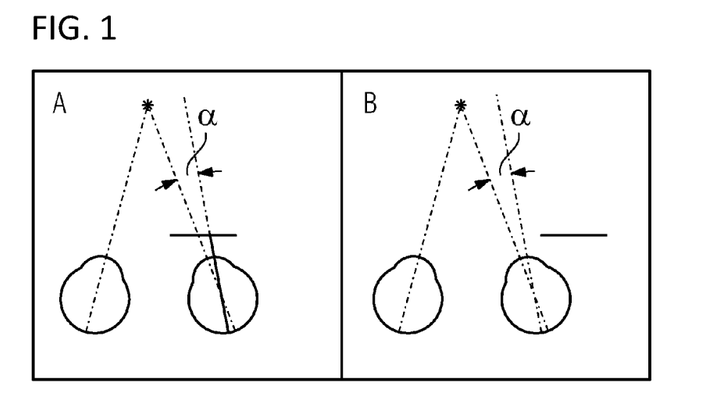
FIG. 1 shows an example of dissociation and regain of bifoveal fixation for individuals with heterophoria.

Heterophoria and heterotropia are anomalies of a binocular vision and are conditions that prevent a person from directing both eyes simultaneously towards to a fixation target. These anomalies can be diagnosed by dissociating the eyes. In the case of heterophoria, for example, if a patient fixates a stationary fixation target and one of the eyes is covered (or dissociated, as it is called), the covered eye will turn by an angle a so that the visual axis no longer passes through the fixation target, as it is shown in panel A of FIG. 1. When the cover is removed, bifoveal fixation is rapidly regained, as shown in panel B of FIG. 1. This behaviour is described in Bennett & Rabbetts 1998, Clinical Visual Optics, $3^{rd}$ edition.

Figure 2:
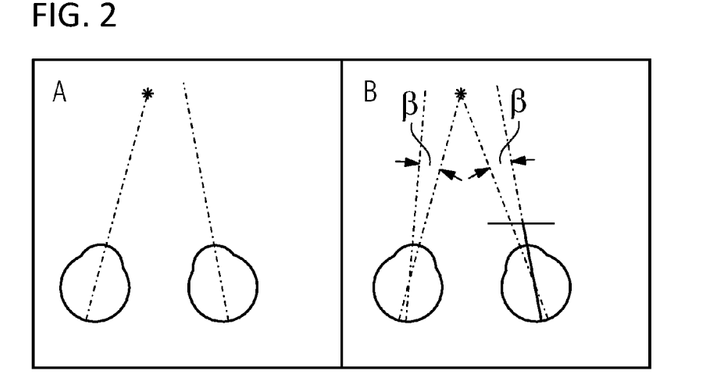
FIG. 2 shows an example of a strabismic eye and of the effect on axis location during dissociation.

In the case of heterotropia, patients do not achieve bifoveal fixation of any object and one of the eyes shows a manifested deviation, even without dissociation, as shown in panel A of FIG. 2. This is also called strabismus. In this case, if the strabismic eye is covered while the patient looks at the fixation point, neither the covered nor the uncovered eye will move, however if the originally fixating eye is covered, the strabismic eye will turn through the angle of misalignment and foveate the fixation point, as it is shown in panel B of FIG. 2. This behaviour is also described in Bennett & Rabbetts 1998, Clinical Visual Optics, $3^{rd}$ edition.

A prevalence of strabismus ranging from 2% to 5% among preschool and school-aged European children has been found in some population-based studies (Frandsen A D. "Occurrence of Squint," Acta Ophthalmol Suppl. 1960, 62, pages 1 to 158, and "Prevalence and risk factors for common vision problems in children: Data from the ALSPAC study," Williams C, Northstone K, Howard M, Harvey I, Harrad R A, Sparrow J M, Br J Ophthalmol., July 2008, 92(7) pages 959 to 964) and similar values have been found in African American populations (Baltimore Vision Screening Project, Preslan M W, Novak A, "Ophthalmology," January 1996, 103(1), pages 105 to 109, and Giordano L, Friedman D S, Repka M X, et al. "Prevalence of strabismus and amblyopia in preschool-aged children: The Baltimore Pediatric Eye Disease Study," Invest Ophthalmol Vis Sci., 2008, 49, E-abstract 1552). In a study of Japanese school children, a prevalence of 1% was found ("The prevalence of strabismus and amblyopia in Japanese elementary school children", Matsuo T, Matsuo C, Ophthalmic Epidemiol., February 2005 12(1), pages 31 to 36, and "Comparison of prevalence rates of strabismus and amblyopia in Japanese elementary school children between the years 2003 and 2005," Matsuo T, Matsuo C, Acta Med Okayama, December 2007, 61(6), pages 329 to 334) and same prevalence of strabismus was found in a population-based sample of native American children in the Kindergarten and first-grade (Garvey 2010 "Prevalence of strabismus among preschool, kindergarten and first-grade Tohono O'Odham children").

Usually, cover tests are performed to determine the presence, classification, and magnitude of an ocular deviation. The test classifies the heterophoria based on the movement of the eye under cover. The classification can be esophoria or exophoria for horizontal movements and hyperphoria or hypophoria for vertical movements. The classification of heterotropia is based on the relative position of the deviating eye and can be esotropia or exotropia for horizontal eye movements and hypertropia or hypotropia for vertical movements. Another method is the so-called MKH ("Mess- und Korrektur nach Hase") measure and correction method which is critically discussed in the community of opticians and ophthalmologists.

Once a heterophoria or heterotropia is diagnosed, it is treated by refractive, prismatic, or orthoptic means. Also surgery is an option, typically the last one.

The current methods of manually diagnosing and treating heterophoria or heterotropia often have the following issues:

Diagnosis, classification and the determination of magnitude of heterophoria or heterotropia lead to a prescription that is verified with the standard optometric methods. This prescription, e.g., a prescription for prismatic glasses, is never tested in a realistic life environment before it is actually applied.

Diagnosis is subjective and based on the experience of the optometrist or examiner.

Determination of the magnitude of correction is estimated by subjective observation of the optometrist and, therefore, the accuracy of the correction also depends on the experience of the examiner.

Determination of oblique deviations is hard to be achieved and, thus, often uncorrected.

Strabismus testing apparatuses as they are described in U.S. Pat. No. 5,094,521 and in CN101147670 (A) can overcome some of these issues. In particular, U.S. Pat. No. 5,094,521 describes a measuring device that allows diagnosing strabismus and suggesting a treatment. However, even when using such testing apparatus, there is no opportunity for testing suggested prisms in a realistic life environment.

WO 2016/139662 A1 discloses a method and a device for measuring strabismus or heterophoria.

EP 3 109 694 A1 discloses a spectacle lens supply system in which a size and an area of clear vision in a progressive power lens is determined according to a level of prescribed fixation disparity amount.

EP 2 856 931 A1 discloses a simulation device for simulating the effect of a spectacle lens where, e.g., prismatic power is considered. In the context of the simulation, a stereoscopic image acquired by imaging cameras is processed to create a simulation image which is supposed to be viewed by the spectacle wearer through the spectacle lens.

SUMMARY

It is an objective of the present disclosure to provide an advantageous apparatus for assisting in establishing a correction for correcting heterotropia or heterophoria by testing a prescription for correcting the heterotropia or heterophoria before the prescription is actually realized. In particular, the disclosure aims to increase the accuracy of a simulation used in the testing.

It is another objective of the present disclosure to provide an advantageous method of operating a computer for assisting in establishing a correction for correcting heterotropia or heterophoria by testing a prescription for correcting the heterotropia or heterophoria before the prescription is actually realized. In particular, the disclosure aims to increase the accuracy of a simulation used in the testing.

The mentioned objectives are achieved by an apparatus and a method of operating a computer as disclosed herein.

An inventive apparatus for assisting in establishing a correction for correcting heterotropia or heterophoria by testing a prescription for correcting the heterotropia or heterophoria before the prescription is actually realized comprises a simulation device with:

An input interface for receiving diagnostic data indicating whether heterotropia or heterophoria is present, classification data indicating which kind of heterotropia or heterophoria is present, magnitude data indicating the magnitude of the heterotropia or heterophoria, and prescription data indicating a prism or prisms suitable for correcting the heterotropia or heterophoria. The simulation device may also comprise a user interface allowing a user to input manually or verbally, or by other suitable means, the diagnosis data, the classification data, the magnitude data, and the prescription data. Moreover, as an addition or as an alternative, the simulation device may comprise a reader for reading a storage medium containing stored diagnosis data, stored classification data, stored magnitude data, and stored prescription data.

A generator unit for generating a right simulation image for the right eye and a left simulation image for the left eye where the right simulation image and the left simulation image each represent the same object or scene looked at by the right eye under a right viewing angle and the left eye under left viewing angle, respectively. The right viewing angle and the left viewing angle are calculated based on the diagnostic data, the classification data, the magnitude data, and the prescription data such that the right viewing angle and/or the left viewing angle correspond to viewing angles which would be achieved by applying the prism or prisms indicated by the prescription data.

A viewing device with separate displays or display sections for the right eye and the left eye of the patient for displaying the simulation image for the right eye and the simulation image for the left eye, respectively.

Using the simulation device offers the possibility to test the prescription in a simulated real life environment before the prescription is actually realized. This allows for correcting the prescription if the patient feels uncomfortable with the prescription before the prisms are actually manufactured. In particular, calculating the right viewing angle and the left viewing angle based on the diagnostic data, the classification data, the magnitude data, and the prescription data such that the right viewing angle and/or the left viewing angle correspond to viewing angles which would be achieved by applying the prism or prisms indicated by the prescription data allows for a individually adapting the simulation image to wearers of spectacle lenses and thus allows for high accuracy in the simulation as compared to simulation devices in which the simulation relies on the view angle of an imaging result obtained by cameras as it is, e.g., the case in the simulation device of EP 2 856 931 A1.

The right simulation image and the left simulation image used in the simulation device may be generated from an image or a video of an object or a scene stored in a memory. As an alternative, the right simulation image and the left simulation image may be generated from a real time video of the environment, e.g., of the examination room. In both cases, a test of the prescription under realistic conditions can be achieved. This is particularly true when a real time image of the examination room is used as basis for the simulation images. However, if for example the examination room is not big enough for simulating an object at a certain distance, the generator unit of the simulation device may use a stored object or scene instead of the real time video of the examination room.

If heterotropia or heterophoria is accompanied by myopia or hyperopia, it is common that the simulation device further comprises a means that allows for correcting the refraction of the patient's eye during the simulation. Such a means may, for example, include a trial frame or at least one wave front manipulator such as a liquid lens, an Alvarez-element, or the like.

In an exemplary embodiment, the disclosed apparatus further comprises a measuring device and an analysing unit.

The measuring device is equipped with
- a means for displaying a fixation target for providing a patient with a target to gaze at;
- a switchable blocking means which allows selectively blocking the sight of the right eye and the left eye when the patient gazes at the fixation target;
- a control unit for switching the switching means according to a blocking sequence describing a sequence of blocking and unblocking the right eye and/or the left eye;
- an eye tracker for tracking the line of sight of at least one of the patient's eyes during the blocking sequence; and
- an output interface for outputting data representing the blocking sequence and data representing the line of the sight of the patient's eyes during the blocking sequence.

The blocking sequence resembles at least one event of blocking and unblocking at least one of the eyes according to a cover test.

As switchable blocking means of the measuring device various implementations are conceivable. In a first implementation, the switchable blocking means comprises at least one cover that can be moved to selectively cover and uncover the right eye or the left eye. In particular, there may be two covers, one for the right eye and one for the left eye, which can be controlled to cover and uncover the right eye and the left eye independently of each other. However, it would also be possible to provide only a single cover which can be switched to cover either the left eye or the right eye and which may also be brought into a neutral position, in which none of the eyes is covered.

In another exemplary embodiment, the switchable blocking means comprise at least one switchable transmission display that is located in front of the patient's eyes. The display can be switched back and forth between a transmissive state and an opaque state. There may be individual displays for each eye, or there may be a single display with left and right sections that can be switched independently.

In yet another exemplary embodiment, the fixation target of the switchable blocking means emits polarized light and the switchable blocking means comprises at least one switchable polarizer located in front of the patient's eyes. The polarizer can be switched back and forth between a first polarizing state and a second polarizing state where the first polarizing state is transmissive for the polarized light of the fixation target, while the second polarizing state is blocking the polarized light of the fixation target. Like in the first two exemplary embodiments discussed above, there may be individual polarizers for each eye, or there may be a single polarizer with switchable sections that can be switched independently where the switchable sections are associated to the left eye and the right eye, respectively.

To allow the eye tracker to accurately track the gazing direction of the patient's eyes the disclosed apparatus may include a fixation unit for fixing the patient's head so that eye movement is prohibited or at least restricted during the measurement. The need for prohibiting or restricting the movement of the patient's eye may be overcome if the measuring device comprises a head tracker for tracking the movement and/or orientation of the patient's head in addition to the eye tracker. In this case, the head tracker establishes the movement and/or orientation while the eye tracker measures the gazing direction so that the gazing direction established by means of the eye tracker can be corrected for changes in the head position and/or the head orientation. However, neither a fixation for the head nor a head tracker is typically provided if the measuring device is integrated into a head mounted device (HMD). By integrating the eye tracker into a head mounted device, the eye tracker is always fixed relative to the head so that a head movement is not reflected in the gazing direction determined by use of the eye tracker. If the measuring device is integrated into a head mounted device, it is advantageous if the simulation device is also integrated into the head mounted device. However, it is generally also possible that only the simulation device is integrated into a head mounted device, while the measuring device is a stationary device which relies on a fixation of the head or a head tracker. The head mounted device may, for example, be based on binocular disparity, holographic projection, projection on the retina, virtual retinal display, etc.

The analysing unit is equipped with:
an input interface that is connected or connectable to the output interface of the measuring device for receiving the data representing the blocking sequence and the data representing the line of the sight of the patient's eyes during the blocking sequence;
an evaluation unit which determines based on the line of sight of the patient's eyes during the blocking sequence deviation data which represents deviations of the line of sight of the patient's eyes from a line of sight necessary for gazing the fixation target;
a diagnostic unit which is coupled to the evaluation unit for receiving the deviation data and which determines from the deviation data the diagnostic data, the classification data, the magnitude data and the prescription data; and
an output interface for outputting the diagnostic data, the classification data, the magnitude data and the prescription data.

The output interface of the analysing unit is connected or connectable to the input interface of the simulation device.

With the described exemplary embodiments of the disclosed apparatus, a means is provided for objectively measuring eye movement in a test for diagnosing heterophoria or heterotropia because the gazing directing of the eye is not estimated by the examiner, but directly measured with the eye tracker. In addition, the accuracy of the measurement does not depend on the experience of the examiner, but only on the measurement accuracy of the eye tracker. Thus, a highly reliable and accurate determination of the line of sight of the patient's eye or eyes during the cover test by means the switchable blocking means can be achieved. In particular, by the use of the eye tracker the measurement device also allows for determining oblique gazing directions which in turn allows for determining oblique heterotropia or heterophoria.

Furthermore, by use of the analysing unit diagnostics of heterophoria and heterotropia as well as the prescription for a treatment can be fully automated. Hence, diagnosing and treating heterotropia and heterophoria is based on objective measurements and does not depend on the examiner's experience. Furthermore, due to the fact that the measuring device is able to also detect oblique ocular deviations, diagnosis and prescription is not restricted to diagnosing and treating horizontal and/or vertical heterotropia or heterophoria.

The disclosure also provides a method of operating a computer for assisting in establishing a correction for correcting heterotropia or heterophoria by testing a prescription for correcting the heterotropia or heterophoria before the prescription is actually realized. The method includes using diagnostic data indicating whether heterotropia or heterophoria is present, classification data indicating which kind of heterotropia or heterophoria is present, magnitude data (m) indicating the magnitude of the heterotropia or heterophoria, and prescription data (p) indicating a prism or prisms suitable for correcting the heterotropia or heterophoria for generating a right simulation image for the right eye and a left simulation image for the left eye where the right simulation image and the left simulation image each represent the same object or scene looked at by the right eye under a right viewing angle and the left eye under left viewing angle, respectively. In the method, the right viewing angle and the left viewing angle are calculated based on the diagnostic data (d), the classification data (c), the magnitude data (m), and the prescription data (p) such that the right viewing angle and/or the left viewing angle correspond to viewing angles which would be achieved by applying the prism or prisms indicated by the prescription data (p). The right simulation image and the left simulation image may be generated from a stored image or video of an object or may be generated from a real time video of the environment. The method also includes outputting the right simulation image and the left simulation image, e.g., to a viewing device.

The inventive method allows using a computer together with a viewing device with separate displays or display sections for the right eye and the left eye of the patient as an apparatus for assisting in establishing a correction for correcting heterotropia or heterophoria.

The method may further include determining, based on data representing a blocking sequence describing a sequence of blocking and unblocking the right eye and/or the left eye and date representing the line of sight of the patient's eyes during the blocking sequence, deviation data which represent deviations of the line of sight of the patient's eyes from a line of sight necessary for gazing at the fixation target during the blocking sequence, and determining the diagnostic data, the classification data, the magnitude data, and the prescription data, from the deviation data. By this exemplary embodiment, the computer can also be used for determining the diagnostic data, the classification data, the magnitude data, and the prescription data, from deviation data.

In addition, the disclosure provides a computer program product including computer readable instructions for performing the method of operating a computer for assisting in establishing a correction for correcting heterotropia or heterophoria. A computer program product may be a computer readable storage medium such as, a USB mass storage device, a flash card, of a DVD. As an alternative, the computer program product may be implemented in form of one or more data packages which is/are made available for downloading form the internet or any other computer network.

BRIEF DESCRIPTION OF THE DRAWINGS

Further features, advantages, and properties of the present disclosure will become clear from the following description of exemplary embodiments in conjunction with the accompanying drawings, wherein.

DESCRIPTION OF EXEMPLARY EMBODIMENTS

Figure 3:
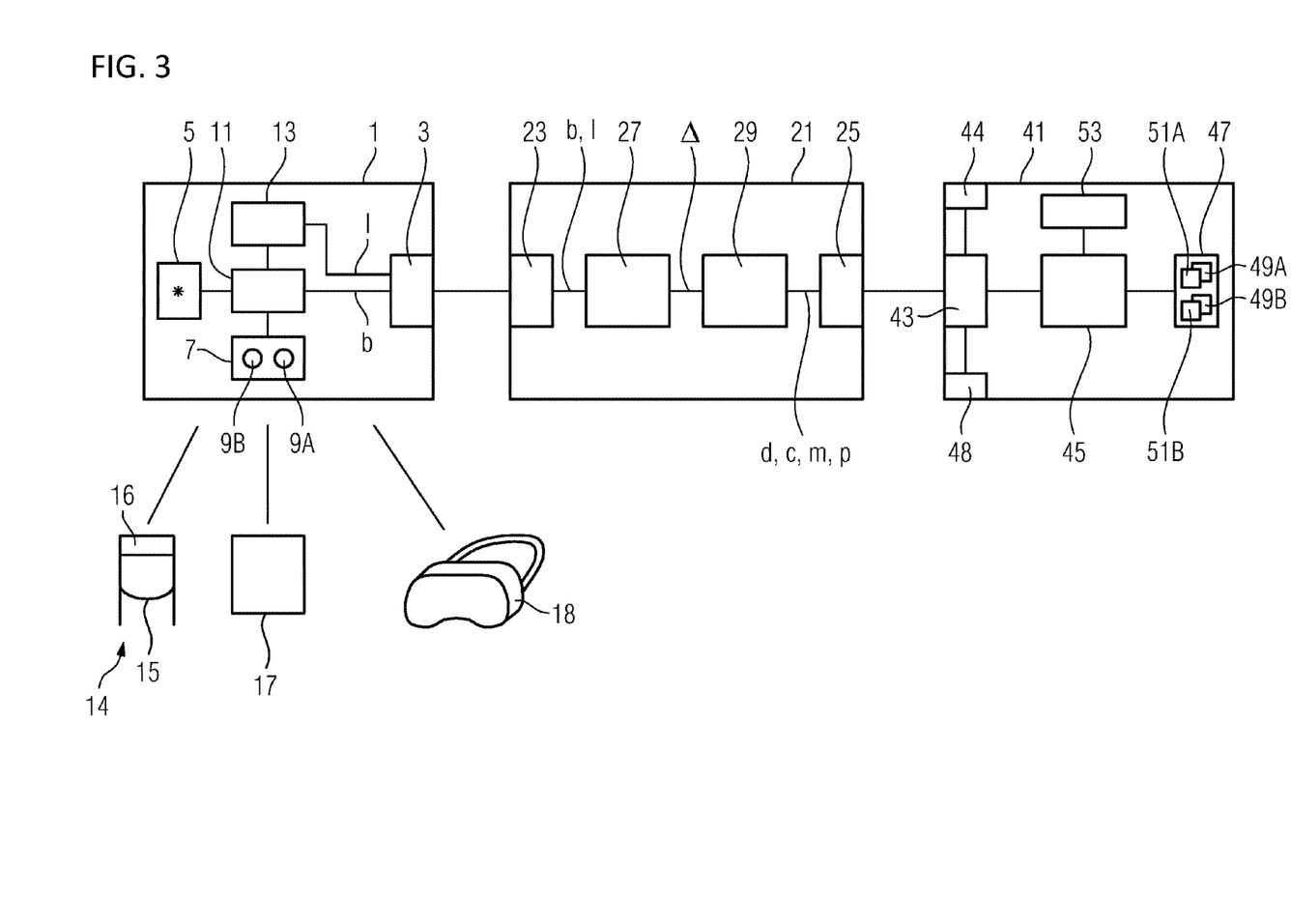
FIG. 3 shows an apparatus for assisting in establishing a correction for correcting heterotropia or heterophoria.

An exemplary embodiment of the present disclosure will be described with respect to FIG. 3, which shows an apparatus for assisting in establishing a correction for correcting heterotropia or heterophoria. The apparatus comprises a measuring device 1, an analysing unit 21, and a simulation device 41. The measuring device 1 and the analysing unit 21 are connected to each other via an output interface 3 of the measuring device and an input interface 23 of the analysing unit 21. In addition, the analysing unit 21 includes an output interface 25 by which it is connected to an input interface 43 of the simulation device 41. The interfaces can be standard interfaces or dedicated interfaces especially designed for connecting the measuring device 1 with the analysing unit 21 and the analysing unit 21 with the simulation device 41, respectively. Moreover, the interfaces may be connected to each other by cable or by wireless means.

The measuring device 1 includes a fixation target 5 to which a patient to be examined directs its gaze. For stopping the head from moving when the patient gazes at the fixation target 5, the measuring device may provide a fixation unit 14 with a support 15 for the patient's chin and a rest 16 for the forehead.

The measuring device 1 further comprises a blocking means 7 which is, in the present exemplary embodiment, a device with moveable covers 9A, 9B, where one of the covers can be moved in front of the patient's right eye while the other one of the covers can be moved in front of the patient's left eye. Movement of the covers 9A, 9B is controlled by control unit 11 which controls moving the covers 9A, 9B in front of the eyes according to a blocking sequence describing a sequence of blocking an unblocking the right eye and/or the left eye of the patient. This blocking sequence includes the covering and uncovering actions of an eye that are necessary for determining heterophoria or heterotropia. While the blocking sequence is performed, an eye tracker 13 which is also part of the measuring device 1 tracks the gazing directions of at least one of the patient's right eye and the patient's left eye. The control unit 11 outputs data b presenting the blocking sequence through the output interface 3 and causes the eye tracker 13 to output data 1 representing the line of sight of the at least one of the patient's eyes during the blocking sequence via the output interface 3.

Figure 4:
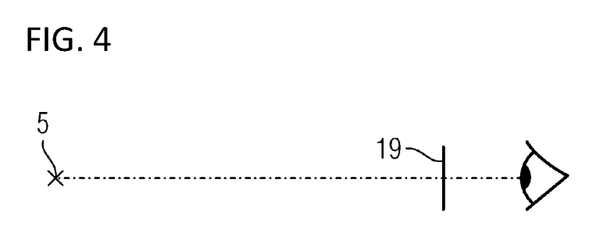
FIG. 4 shows an exemplary embodiment detail of the apparatus shown in FIG. 3.
Figure 5:
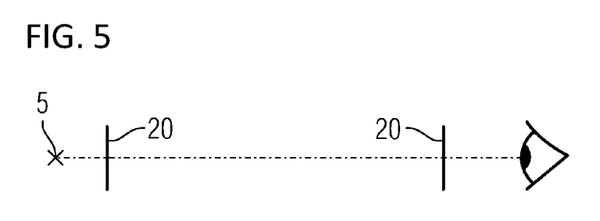
FIG. 5 shows an alternative exemplary embodiment of the detail shown in FIG. 4.

Although the switchable blocking means 7 which allows selectively blocking the sight of the right eye and the left eye when the patient gazes at the fixation target 5 comprises two covers 9A, 9B in the present exemplary embodiment, other implementations of the blocking device are possible. For example, instead of moveable covers 9A, 9B, liquid crystal displays 19 may be placed before the patient's eyes which can be switched by the control unit 11 into a transmissive state and an opaque state (FIG. 4). When an eye shall be covered (dissociate) the respective display 19 becomes opaque. In a still further exemplary embodiment, the switchable blocking means can be realized by the use of polarizing filters 20 in front of the patient's eyes if the light of the fixation target 5 is polarized, e.g., by a further polarizing filter 20 in front of the light source of the fixation target 5 (FIG. 5). If, for example, the polarizing filter 20 in front of the light source of the fixation target 5 polarizes the light linearly in a first direction, the polarizing filter 20 in front of the patient's eye can be switched between polarizing states perpendicular and parallel to the polarizing direction of the polarizer in front of the fixation target 5 so that the polarized light from the fixation target 5 can pass the polarizing filter 20 in front of the patient's eye (the polarising filters in front of the light source and in front of the eye are oriented parallel to each other) or is blocked the polarizing filter 20 in front of the patient's eye (the polarising filters in front of the light source and in front of the eye are oriented perpendicular to each other).

As has already been mentioned, during the measurement the head of the patient is kept fixed by the chin support 15 and the rest 16 for the forehead. However, if the measuring device 1 is equipped with a head tracker 17 which tracks the position and/or orientation of the head a fixation unit 14 for fixing the patient's head is not necessary because the gazing direction measured by the eye tracker 13 can be corrected for taking into account the head position and/or head orientation given by the result of the measurement performed by the head tracker 17.

A further possibility is to integrate the measuring device into 1 a head mounted device 18 like a helmet or goggles like structure which include the switchable blocking means 7 and the eye tracker 13, for example. Since the orientation of the head mounted device 18 is fixed relative to the head, a fixation unit 14 or a head tracker 17 are not necessary during the measurement of the gazing direction of the patient's eyes.

The analysing unit 21 receives from measuring device 1 via the input interface 23 the data b representing the blocking sequence and the data 1 representing the line of sight of at least one of the patient's eyes during the blocking sequence. In the analysing unit 21, an evaluation unit 27 evaluates the data b representing the blocking sequence and the data 1 representing the line of sight to determine whether the line of sight of the patient's eyes measured during the blocking sequence deviates from the line of sight necessary for gazing at the fixation target. The determined deviation is then output from the evaluation unit 27 in form of a deviation data Δ.

A diagnostic unit 29 of the analysing unit 21 receives the deviation data Δ and determines from the deviation data Δ, diagnostic data d, classification data c, magnitude data m, and prescription data p. The diagnostic data d represents whether or not heterotropia or heterophoria is present, the classification data c indicates which kind of heterotropia or heterophoria is present, the magnitude data m indicates the magnitude of the heterotropia or heterophoria, and the prescription data p indicates a prism or prisms suitable for correcting the heterotropia or heterophoria which has been found to be present with a certain direction and magnitude. The diagnostic data d, the classification data c, the magnitude data m, and the prescription data p is then output from the analysing unit 21 through the output interface 25.

The data d, c, m, and p output through the output interface 25 of the analysing unit 21 is received by the input interface 43 of the simulation device 41. The simulation device 41 includes a generator unit 45 which generates a stereoscopic simulation image, i.e., a right simulation image for the right eye and a left simulation image for the left eye, where both simulation images represent the same object or scene under a right eye viewing angle and a left eye viewing angle, respectively. The right eye viewing angle and the left eye viewing angle are calculated based on the diagnostic data d, the classification data c, the magnitude data m, and the prescription data p such that the right viewing angle and/or the left viewing angle correspond to the viewing angles achieved with the prism or prisms indicated by the prescription data. In other words, to simulate the effect of the prism or prisms without using an actual prism, the viewing angle of the simulation image presented to the affected eye or eyes is/are calculated such as to simulate the line of sight which would be achieved with the prism or prisms indicated in the prescription data p installed in front of the affected eye. For example, in the case shown in FIG. 2, the diagnostic data d would indicate heterotropia, the classification data c would indicated a deviation of the strabismic eye which directs away from the other eye, the magnitude data m would give the angle β, and the prescription data p would describe a prism suitable for correcting the line of sight of the affected eye so that, with the prism or prisms installed, both eyes would gaze at the fixation target.

By use of the simulation device 41, the effect of the prism or prisms can be simulated before the prism or prisms is/are manufactured and, in case the patient feels uncomfortable with the result of the simulation, the diagnostics can be reviewed and the prism or prisms can be amended if the review reveals that a different kind of prism or prisms would lead to a result more comfortable for the patient.

For presenting the stereoscopic simulation image to the patient, the simulation device 41 comprises a viewing device 47, which, in the present exemplary embodiment, includes two displays 49A, 49B, where one of the displays is provided for the right eye and the other one is provided for the left eye. The viewing device 47 can be located in a stationary optical instrument or in a head mounted device. In particular, the viewing device may be integrated in the same optical instrument or the same head mounted device as the measuring device 1.

The right and left simulation images may be generated based on images or videos of objects or scenes stored in a memory 53 of the simulation device 41. When using images or videos stored in a memory 53, a large number of objects or scenes can be presented to the patient. Hence, the right and left simulation images can closely meet the needs and preferences of a patient. On the other hand, instead of using videos or images stored in the memory 53, a live video of the examination room could be used for generating the stereoscopic simulation image. This way of generating the simulation image allows presenting a very realistic image impression to the patient.

If the patient does not only show heterophoria or heterotropia but is also nearsighted (myopic) or farsighted (hyperopic), the lack of refraction of the patient's eyes needs also to be corrected. To this end, the viewing device typically also includes a refraction correcting device, which may be in the simplest case be a trial frame that allows putting lenses 51A, 51B in front the patient's eyes. However, a kind of wave front manipulator which allows introducing a defocus could be used instead of a trial frame. In this case, a wave front manipulator would be present in front of each eye. As wave front manipulators, liquid lenses, Alvarez-elements or the like could be used. By varying the liquid lens or the Alvarez-element, the necessary refraction correction could be provided.

Although the simulation device 41 has been described to receive the diagnostic data d, the classification data c, the magnitude data m, and the prescription data p from the analysing unit 21, the simulation device is, in the present exemplary embodiment, also equipped with a user interface 44 allowing for manually or verbally inputting data relating to a diagnosis indicating whether heterotropia or heterophoria is present, a classification indicating which kind of heterotropia or heterophoria is present, a magnitude indicating the magnitude of the heterotropia or heterophoria, and a prescription indicating a prism or prisms suitable for correcting the heterotropia or heterophoria. The user interface 44 may include a keyboard, a touchpad or touchscreen, a speech recognition unit, or any other unit that allows a user to input the mentioned data. In addition, in the present exemplary embodiment, the simulation device 41 also comprises a reader 48 for reading a storage medium containing stored data relating to a diagnosis indicating whether heterotropia or heterophoria is present, a classification indicating which kind of heterotropia or heterophoria is present, a magnitude indicating the magnitude of the heterotropia or heterophoria, and a prescription indicating a prism or prisms suitable for correcting the heterotropia or heterophoria. The storage medium may be any non-transitory storage medium suitable for storing the mentioned data, for example a memory stick, a memory card, a DVD, etc.

In another exemplary embodiment of the disclosure, the tasks of the generator unit 45, the input interface 43, and the user interface 44 are realized by a computer running software implementing a method of using the computer for assisting in establishing a correction for correcting heterotropia or heterophoria. By running the software, the computer uses the diagnostic data (d), the classification data (c), the magnitude data (m), and the prescription data (p) to generate a right simulation image for the right eye and a left simulation image for the left eye. The right simulation image and the left simulation image each represent the same object or scene looked at by the right eye under a right viewing angle and the left eye under left viewing angle, respectively, where the right viewing angle and the left viewing angle are calculated based on the diagnostic data (d), the classification data (c), the magnitude data (m), and the prescription data (p) such that the right viewing angle and/or the left viewing angle correspond to viewing angles which would be achieved by applying the prism or prisms indicated by the prescription data (p). The computer then outputs the right simulation image and the left simulation image to a viewing device 47 which may be a viewing device as used in the first exemplary embodiment.

In a further exemplary embodiment of the disclosure, the computer also performs the tasks of the analysing unit 21. In this exemplary embodiment, the computer running the software also determines, based on the data representing the line of sight of the patient's eyes during a blocking sequence and data representing the blocking sequence, deviation data (Δ) which represent deviations of the line of sight of the patient's eyes from a line of sight of a non-heterotropic or non-heterophoric eye gazing at the fixation target (5) during the blocking sequence. The computer then determines the diagnostic data (d), the classification data (c), the magnitude data (m), and the prescription data (p), from deviation data (Δ).

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the inventive concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

REFERENCE NUMERALS 1 measuring device
3 output interface
5 fixation target
7 blocking means
9A, B cover
11 control unit
13 eye tracker
14 fixation unit
15 chin support
16 rest for forehead
17 heat tracker
18 head mounted device
21 analysing unit
23 input interface
25 output interface
27 evaluation unit
29 diagnostic unit
41 simulation device
43 input interface
44 user interface
45 generator unit
47 viewing device
48 reader
49A, B display
51A, B refraction correcting device
53 memory
b data representing blocking sequence
l data representing line of sight
Δ deviation data
d diagnostic data
c classification data
m magnitude data
p prescription data

The invention claimed is:

1. An apparatus for assisting in establishing a correction for correcting heterotropia or heterophoria by testing a prescription for correcting the heterotropia or heterophoria of a patient before the prescription is actually realized, the apparatus comprising:
   a simulation device having:
      an input interface configured to receive prescription data indicating a prism to be tested for a suitability of the prism to correct the heterotropia or the heterophoria;
      a generator unit configured to generate a right simulation image for a right eye and a left simulation image for a left eye of the patient, wherein the right simulation image and the left simulation image each represent a same object or scene looked at by the right eye under a right viewing angle and the left eye under a left viewing angle, respectively, and wherein the right viewing angle and the left viewing angle are calculated based on the prescription data such that at least one of the right viewing angle or the left viewing angle corresponds to viewing angles which would be achieved by applying the prism indicated by the prescription data; and
      a viewing device having separate displays or display sections for the right eye and the left eye, the viewing device being configured to display the right simulation image for the right eye and the left simulation image for the left eye, respectively,
   wherein the input interface is configured to receive, in addition to the prescription data, diagnostic data indicating whether the heterotropia or the heterophoria is present, classification data indicating a kind of the heterotropia or the heterophoria being present, and magnitude data indicating a magnitude of the heterotropia or the heterophoria,
   wherein the right viewing angle and the left viewing angle are, in addition to the prescription data, calculated based on the diagnostic data, the classification data, and the magnitude data,
   wherein the simulation device further includes a trial frame, at least one wave front manipulator, or the trial frame and the at least one wave front manipulator, and
   wherein the trial frame, the at least one wave front manipulator, or the trial frame and the at least one wave front manipulator are configured to correct a refraction of the right eye and the left eye.

2. The apparatus as claimed in claim 1, further comprising at least one of:
   a means for generating the right simulation image and the left simulation image from an image or a video of an object or a scene stored in a memory; or
   a means for generating the right simulation image and the left simulation image from a real time video of an environment of the apparatus.

3. The apparatus as claimed in claim 1, wherein the simulation unit further comprises at least one of:

a user interface configured to input the diagnostic data, the classification data, the magnitude data, and the prescription data, or a reader configured to read stored diagnostic data, stored classification data, stored magnitude data, and stored prescription data from a non-transitory computer storage medium.

4. The apparatus as claimed in claim 1, further comprising:

a measuring device having:

a means for displaying a fixation target configured to provide the patient with a target to gaze at;

a switchable blocking means configured to selectively block a sight of the right eye or a sight the left eye when the patient gazes at the fixation target;

a control unit configured to switch the switching means according to a blocking sequence defining a sequence of blocking and unblocking of at least one of the right eye or the left eye;

an eye tracker configured to track a line of sight of the at least one of the right eye or the left eye during the blocking sequence;

an output interface configured to output blocking data representing the blocking sequence and line of sight data representing the line of sight of the at least one of the right eye or the left eye during the blocking sequence; and an analysing unit having:

an input interface that is connected or connectable to the output interface of the measuring device and configured to receive the blocking data representing the blocking sequence and the line of sight data representing the line of sight of the right eye and the left eye during the blocking sequence, an evaluation unit configured to determine, based on the line of sight of the right eye and the line of sight of the left eye during the blocking sequence, deviation data representing deviations of the line of sight of the right eye or the line of sight of the left eye from a line of sight of a non-heterotropic or non-heterophoric eye gazing at the fixation target; and a diagnostic unit coupled to the evaluation unit configured to receive the deviation data and determine the diagnostic data, the classification data, the magnitude data, and the prescription data from the from deviation data; and an output interface configured to output the diagnostic data, the classification data, the magnitude data, and the prescription data, wherein the output interface of the analysing unit is connected or connectable to the input interface of the simulation device.

5. The apparatus as claimed in claim 4, wherein the switchable blocking means comprises at least one of:

a cover configured to selectively cover the right eye or the left eye; or at least one switchable transmission display configured to be locatable in front of the right eye or the left eye and to be switched between a transmissive state and an opaque state.

6. The apparatus as claimed in claim 4, wherein the fixation target emits polarised light, wherein the switchable blocking means further includes at least one switchable polariser locatable in front of the right eye or the left eye, and wherein the at least one switchable polariser can be switched between a first polarising state being transmissive for the polarised light emitted by the fixation target and a second polarising state blocking the polarised light emitted by the fixation target.

7. The apparatus as claimed in claim 4, wherein the measuring device further comprises:

a fixation unit configured to fix a patient's head; or a head tracker for tracking a movement of the patient's head.

8. The apparatus as claimed in claim 1, wherein at least one of the measuring device or the viewing device of the simulation device is integrated in a head mounted device.

9. A method of operating a computer for assisting in establishing a correction for correcting heterotropia or heterophoria by testing a prescription for correcting the heterotropia or the heterophoria before the prescription is actually realized, the method comprising:

providing a simulation device having:

an input interface configured to receive prescription data indicating a prism to be tested for a suitability of the prism to correct the heterotropia or the heterophoria and to receive diagnostic data indicating whether the heterotropia or the heterophoria is present, classification data indicating which kind of the heterotropia or the heterophoria is present, and magnitude data indicating a magnitude of the heterotropia or the heterophoria;

a generator unit configured to generate a right simulation image for a right eye and a left simulation image for a left eye;

a viewing device having separate displays or display sections for the right eye and the left eye and being configured to display the right simulation image to the right eye and the left simulation image to the left eye, respectively; and a trial frame, at least one wave front manipulator, or the trial frame and the at least one wave front manipulator;

receiving the prescription data indicating the prism to be tested for the suitability of the prism to correct the heterotropia or the heterophoria via the input interface;

receiving the diagnostic data indicating whether the heterotropia or the heterophoria is present, the classification data indicating which kind of the heterotropia or the heterophoria is present, and the magnitude data indicating the magnitude of the heterotropia or the heterophoria via the input interface;

calculating, with the simulation device, the right viewing angle and the left viewing angle based on the prescription data, such that at least one of the right viewing angle or the left viewing angle corresponds to a viewing angle which would be achieved by applying the prism indicated by the prescription data, the diagnostic data, the classification data, and the magnitude data;

generating the right simulation image for the right eye and the left simulation image for the left eye, wherein the right simulation image and the left simulation image each represent a same object or a same scene looked at by the right eye under a right viewing angle and the left eye under a left viewing angle, respectively; and outputting the right simulation image and the left simulation image to the respective separate displays or display sections of the viewing device.

10. The method as claimed in claim 9, further comprising:

determining, based on blocking data representing a blocking sequence describing a sequence of blocking and unblocking at least one of the right eye or the left eye and data representing the line of sight of the at least one of the right eye or the left eye during the blocking sequence, deviation data representing a deviation of the line of sight of the at least one of the right eye or the left eye from a line of sight of a non-heterotropic eye or a non-heterophoric eye gazing at the fixation target during the blocking sequence, and determining the diagnostic data, the classification data, the magnitude data, and the prescription data from the deviation data.

11. The method as claimed in claim 9, further comprising:
generating the right simulation image and the left simulation image from a stored image or a stored video of an object.

12. The method as claimed in claim 9, further comprising:
generating the right simulation image and the left simulation image from a real time video of an environment of the apparatus.

13. A computer program product stored on a non-transitory storage medium, the program including computer readable instructions for performing the method claimed in claim 9.

* * * * *